United States Patent
Kiyomoto et al.

(10) Patent No.: US 11,725,072 B2
(45) Date of Patent: Aug. 15, 2023

(54) ALKYL-MODIFIED CARBOXYL GROUP-CONTAINING COPOLYMER, THICKENER CONTAINING SAID COPOLYMER, AND METHOD FOR PREPARING SAID COPOLYMER

(71) Applicant: SUMITOMO SEIKA CHEMICALS CO., LTD., Hyogo (JP)

(72) Inventors: Rie Kiyomoto, Himeji (JP); Satoshi Nishiguchi, Tokyo (JP); Ryosuke Murakami, Himeji (JP); Naoyuki Hashimoto, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 587 days.

(21) Appl. No.: 16/643,437

(22) PCT Filed: Aug. 24, 2018

(86) PCT No.: PCT/JP2018/031290
§ 371 (c)(1),
(2) Date: Feb. 28, 2020

(87) PCT Pub. No.: WO2019/044679
PCT Pub. Date: Mar. 7, 2019

(65) Prior Publication Data
US 2020/0207894 A1 Jul. 2, 2020

(30) Foreign Application Priority Data
Aug. 30, 2017 (JP) .................. 2017-165399

(51) Int. Cl.
| | | |
|---|---|---|
| C08F 220/06 | (2006.01) | |
| C09K 23/52 | (2022.01) | |
| A61K 8/81 | (2006.01) | |
| C08F 2/08 | (2006.01) | |
| A61Q 19/00 | (2006.01) | |
| C08L 33/02 | (2006.01) | |

(52) U.S. Cl.
CPC ............ C08F 220/06 (2013.01); C08L 33/02 (2013.01); C08L 2201/10 (2013.01)

(58) Field of Classification Search
CPC .................. C08F 220/06; C08F 220/1818
See application file for complete search history.

(56) References Cited

U.S. PATENT DOCUMENTS

| | | |
|---|---|---|
| 3,915,921 A | 10/1975 | Schlatzer, Jr. |
| 3,940,351 A | 2/1976 | Schlatzer, Jr. |
| 4,509,949 A | 4/1985 | Huang et al. |
| 2009/0227751 A1 | 9/2009 | Yoshinaka et al. |
| 2010/0130711 A1 | 5/2010 | Chu et al. |
| 2014/0142269 A1 | 5/2014 | Takemori et al. |
| 2017/0291976 A1 | 10/2017 | Nishiguchi et al. |

FOREIGN PATENT DOCUMENTS

| | | |
|---|---|---|
| EP | 1950231 B1 | 8/2015 |
| EP | 3205694 A1 | 8/2017 |
| JP | S51-6190 A | 1/1976 |
| JP | S59-232107 A | 12/1984 |
| JP | 2009-084502 A1 | 4/2009 |
| JP | 2011-105833 A | 6/2011 |
| JP | 2012-007010 A | 1/2012 |
| JP | 2014-047241 A | 3/2014 |
| WO | WO 2007/055354 A1 | 5/2007 |
| WO | WO 2013/008627 A1 | 1/2013 |
| WO | WO 2016/056591 A1 | 4/2016 |

OTHER PUBLICATIONS

English Translation of ISR of PCT/JP2018/031290, dated Sep. 18, 2018.
Extended European Search Report in EP Patent Application No. 18851230.5 dated Apr. 29, 2021.
Indian Office Action in Indian Patent Application No. 202017007443 dated Jul. 28, 2021.

*Primary Examiner* — Irina S Zemel
*Assistant Examiner* — Jeffrey S Lenihan
(74) *Attorney, Agent, or Firm* — Knobbe Martens Olson & Bear LLP

(57) ABSTRACT

Provided is an alkyl-modified carboxyl group-containing copolymer with which a neutralized viscous liquid can be prepared which has excellent dispersibility in water, has a viscosity that does not change greatly regardless of addition of an electrolyte, and has high transparency in the presence of an electrolyte. This alkyl-modified carboxyl group-containing copolymer contains: 100 parts by mass of a (meth) acrylic acid; 1.5-4.5 parts by mass of a (meth)acrylic acid alkyl ester, in which an alkyl group has 18-24 carbon atoms; and 0-0.1 parts by mass of a compound having two or more ethylenically unsaturated groups, wherein the copolymer contains 1.5-4.5 parts by mass of a nonionic surfactant.

10 Claims, No Drawings

ALKYL-MODIFIED CARBOXYL GROUP-CONTAINING COPOLYMER, THICKENER CONTAINING SAID COPOLYMER, AND METHOD FOR PREPARING SAID COPOLYMER

TECHNICAL FIELD

The present invention relates to an alkyl-modified carboxyl group-containing copolymer, a thickener containing the copolymer, and a method for preparing the copolymer.

BACKGROUND ART

Conventionally, various copolymers have been known as copolymers of (meth)acrylic acid and alkyl (meth)acrylate ester, usable in a thickener for cosmetics, a moisture-retaining agent for poultice, an emulsifying agent, and a suspension stabilizing agent. For example, a copolymer prepared by reacting a specified amount of an olefinic unsaturated carboxylic acid monomer, a specified amount of an alkyl (meth)acrylate ester (of which alkyl group has 8 to 30 carbon atoms), and a crosslinking agent (see Patent Document 1); a copolymer prepared by reacting a specified amount of an olefinic unsaturated carboxylic acid monomer, a specified amount of an alkyl (meth)acrylate ester (of which alkyl group has 8 to 30 carbon atoms), and a crosslinking agent (see Patent Document 2); and the like have been known. These copolymers of (meth)acrylic acid and alkyl (meth)acrylate ester can be used in each of the applications mentioned above by usually dissolving the copolymer in water or the like, and thereafter neutralizing the solution with an alkali to prepare a neutralized viscous liquid having a concentration of about 0.1 to 1% by mass.

When an electrolyte used as various raw materials and an additive constituting the manufactured articles is co-present, there are some disadvantages that even at its relatively low concentration, the neutralized viscous liquid has a lowered viscosity or a lowered light transmittance and that a part of the copolymer is precipitated.

For this problem, a copolymer prepared by reacting (meth)acrylic acid, alkyl (meth)acrylate ester (of which alkyl group has 18 to 24 carbon atoms), and a crosslinking agent (see Patent Document 3) is developed as a thickener which is able to produce a neutralized viscous liquid which has a high viscosity and a high transmittance and has moist textures without stickiness even in the presence of a relatively high concentration of electrolytes. However, the copolymer has disadvantages that solubility in water is poor and that a viscosity difference of the neutralized viscous liquid is very large depending on presence or absence of an electrolyte, making it difficult to control the viscosity.

PRIOR ART DOCUMENTS

Patent Documents

Patent Document 1: Japanese Patent Laid-open Publication No. 59-232107
Patent Document 2: Japanese Patent Laid-open Publication No. 51-6190
Patent Document 3: International Publication No. 2007/055354

SUMMARY OF THE INVENTION

Problems to be Solved by the Invention

An object of the present invention is to provide an alkyl-modified carboxyl group-containing copolymer with which a neutralized viscous liquid can be prepared which has excellent dispersibility in water, has a viscosity that does not change greatly regardless of addition of an electrolyte, and has high transparency in the presence of an electrolyte.

Means for Solving the Problem

The inventors of the present invention conducted a diligent study to solve the aforementioned problem. As a result, it has been found that a neutralized viscous liquid which has excellent dispersibility in water, has a viscosity that does not change greatly regardless of addition of an electrolyte, and has high transparency in the presence of an electrolyte can be prepared with an alkyl-modified carboxyl group-containing copolymer which is a copolymer of 100 parts by mass of a (meth)acrylic acid, 1.5 to 4.5 parts by mass of an alkyl (meth)acrylate ester having an alkyl group having 18 to 24 carbon atoms, and 0 to 0.1 parts by mass of a compound having two or more ethylenically unsaturated groups and contains 1.5 to 4.5 parts by mass of a nonionic surfactant.

In summary, the present invention provides aspects of the invention comprising the following features:

Item 1.

An alkyl-modified carboxyl group-containing copolymer being a copolymer of 100 parts by mass of a (meth)acrylic acid, 1.5 to 4.5 parts by mass of an alkyl (meth)acrylate ester having an alkyl group having 18 to 24 carbon atoms, and 0 to 0.1 parts by mass of a compound having two or more ethylenically unsaturated groups, the alkyl-modified carboxyl group-containing copolymer comprising 1.5 to 4.5 parts by mass of a nonionic surfactant.

Item 2.

The alkyl-modified carboxyl group-containing copolymer according to Item 1, wherein a light transmittance X of a 1% by mass neutralized viscous liquid of the alkyl-modified carboxyl group-containing copolymer is 90% or more.

Item 3.

The alkyl-modified carboxyl group-containing copolymer according to Item 1 or 2, wherein a light transmittance Y of an electrolyte-containing 1% neutralized viscous liquid prepared by adding 1 part by mass of sodium chloride to 100 parts by mass of the 1% by mass neutralized viscous liquid of the alkyl-modified carboxyl group-containing copolymer is 90% or more.

Item 4.

The alkyl-modified carboxyl group-containing copolymer according to any one of Items 1 to 3, wherein a viscosity A of the 1% by mass neutralized viscous liquid of the alkyl-modified carboxyl group-containing copolymer is 5,000 mPa·s or more at 25° C.

Item 5.

The alkyl-modified carboxyl group-containing copolymer according to any one of Items 1 to 4, wherein a viscosity ratio (viscosity B/viscosity A) of a viscosity B of an electrolyte-containing 1% neutralized viscous liquid, prepared by adding 1 part by mass of sodium chloride to 100 parts by mass of the 1% by mass neutralized viscous liquid of the alkyl-modified carboxyl group-containing copolymer, to the viscosity A of the 1% by mass neutralized viscous liquid is in a range of 0.5 to 2.0 at 25° C.

Item 6.

The alkyl-modified carboxyl group-containing copolymer according to any one of Items 1 to 5, wherein an absolute value |viscosity A-viscosity B| of a difference between the viscosity A of the 1% by mass neutralized viscous liquid of the alkyl-modified carboxyl group-containing copolymer and the viscosity B of the electrolyte-containing 1% neutralized viscous liquid prepared by adding 1 part by mass of sodium chloride to 100 parts by mass of the 1% by mass neutralized viscous liquid is 10,000 mPa·s or less.

Item 7.

The alkyl-modified carboxyl group-containing copolymer according to any one of Items 1 to 6, wherein the compound having two or more ethylenically unsaturated groups is at least one selected from the group consisting of pentaerythritol polyallyl ether, diethylene glycol diallyl ether, polyethylene glycol allyl ether, and polyallyl saccharose.

Item 8.

The alkyl-modified carboxyl group-containing copolymer according to any one of Items 1 to 7, being in a form of fine particles.

Item 9.

A thickener comprising the alkyl-modified carboxyl group-containing copolymer according to any one of Items 1 to 8.

Item 10.

A method for preparing the alkyl-modified carboxyl group-containing copolymer according to any one of Items 1 to 8, the method comprising copolymerizing a (meth) acrylic acid, an alkyl (meth)acrylate ester having an alkyl group having 18 to 24 carbon atoms, and optionally a compound having two or more ethylenically unsaturated groups in the presence of a nonionic surfactant.

Advantages of the Invention

According to the present invention, it is possible to provide an alkyl-modified carboxyl group-containing copolymer with which a neutralized viscous liquid can be prepared which has excellent dispersibility in water, has a viscosity that does not change greatly regardless of addition of an electrolyte, and has high transparency in the presence of an electrolyte.

Embodiments of the Invention

The alkyl-modified carboxyl group-containing copolymer of the present invention is a copolymer of 100 parts by mass of a (meth)acrylic acid, 1.5 to 4.5 parts by mass of a (meth)acrylic acid alkyl ester having an alkyl group having 18 to 24 carbon atoms, and 0 to 0.1 parts by mass of a compound having two or more ethylenically unsaturated groups. This alkyl-modified carboxyl group-containing copolymer contains 1.5 to 4.5 parts by mass of a nonionic surfactant. The alkyl-modified carboxyl group-containing copolymer of the present invention has suitable dispersibility in water. Hereinafter, the alkyl-modified carboxyl group-containing copolymer of the present invention, a thickener containing the copolymer, and a method for preparing the copolymer will be described in detail.

In the present invention, "acrylic acid" and "methacrylic acid" are generally referred to as "(meth)acrylic acid". In the present invention, the "neutralized viscous liquid" refers to an alkyl-modified carboxyl group-containing copolymer neutralized by mixing an alkali component (for example, sodium hydroxide) with an aqueous dispersion of the alkyl-modified carboxyl group-containing copolymer of the present invention so that pH of the aqueous dispersion of the alkyl-modified carboxyl group-containing copolymer is 6.5 to 7.5. Further, the "1% by mass neutralized viscous liquid" refers to a neutralized viscous liquid in which the ratio of the alkyl-modified carboxyl group-containing copolymer of the present invention is 0.9 to 1% by mass. Furthermore, the "electrolyte-containing 1% neutralized viscous liquid" refers to a neutralized viscous liquid prepared by adding 1 part by mass of sodium chloride to 100 parts by mass of a 1% by mass neutralized viscous liquid.

The alkyl-modified carboxyl group-containing copolymer of the present invention is a copolymer of 100 parts by mass of a (meth)acrylic acid, 1.5 to 4.5 parts by mass of an alkyl (meth)acrylate ester having an alkyl group having 18 to 24 carbon atoms, and 0 to 0.1 parts by mass of a compound having two or more ethylenically unsaturated groups, and the copolymer contains 1.5 to 4.5 parts by mass of a nonionic surfactant. As will be described later, the alkyl-modified carboxyl group-containing copolymer of the present invention can be prepared by copolymerizing acrylic acid, an alkyl (meth)acrylate ester having an alkyl group having 18 to 24 carbon atoms, and a compound having two or more ethylenically unsaturated groups, in the presence of a predetermined amount of nonionic surfactant such that the predetermined ratio is given.

In the present invention, as (meth)acrylic acid, at least one of acrylic acid and methacrylic acid can be used, and acrylic acid is preferred.

An alkyl (meth)acrylate ester having an alkyl group having 18 to 24 carbon atoms is an ester obtained by reacting (meth)acrylic acid with a higher alcohol having an alkyl group having 18 to 24 carbon atoms. Specific examples include stearyl (meth)acrylate, eicosanyl (meth)acrylate, behenyl (meth)acrylate, and tetracosanyl (meth)acrylate. Among them, stearyl methacrylate, eicosanyl methacrylate, behenyl methacrylate, and tetracosanyl methacrylate are suitably used from the viewpoint of suitably preparing a neutralized viscous liquid which has excellent dispersibility in water, has a viscosity that does not change greatly regardless of addition of an electrolyte, and has high transparency in the presence of an electrolyte.

In the alkyl-modified carboxyl group-containing copolymer of the present invention, an alkyl (meth)acrylate ester in which an alkyl group constituting a monomer has 18 to 24 carbon atoms may be used alone or in combination of two or more types. In the copolymerization using two or more types of alkyl (meth)acrylate ester having an alkyl group having 18 to 24 carbon atoms, for example, it is possible to use the trade name of BLEMMER VMA-70, manufactured by NOF Corporation (a mixture containing 10 to 20 parts by mass of stearyl methacrylate, 10 to 20 parts by mass of eicosanyl methacrylate, 59 to 80 parts by mass of behenyl methacrylate, and 1 part by mass or less of tetracosanyl methacrylate).

In the alkyl-modified carboxyl group-containing copolymer of the present invention, the ratio of the alkyl (meth) acrylate ester having an alkyl group having 18 to 24 carbon atoms is 1.5 to 4.5 parts by mass to 100 parts by mass of (meth)acrylic acid. From the viewpoint of suitably preparing a neutralized viscous liquid which has excellent dispersibility in water, has a viscosity that does not change greatly regardless of addition of an electrolyte, and has high transparency in the presence of an electrolyte, the lower limit of the ratio of the alkyl (meth)acrylate ester having an alkyl group having 18 to 24 carbon atoms is 1.5 parts by mass to 100 parts by mass of (meth)acrylic acid, and an upper limit thereof is 4.5 parts by mass or less, preferably 3.5 parts by mass or less, more preferably 3.0 parts by mass or less. The range for the ratio is preferably 1.5 to 3.5 parts by mass, more preferably 1.5 to 3.0 parts by mass.

In the alkyl-modified carboxy group-containing copolymer of the present invention, a compound having two or more ethylenically unsaturated groups which are monomer components contained as necessary is a compound having two or more ethylenically unsaturated groups having polymerizability. Preferable examples include pentaerythritol polyallyl ethers such as pentaerythritol diallyl ether, pentaerythritol triallyl ether, and pentaerythritol tetraallyl ether, diethylene glycol diallyl ether, polyethylene glycol allyl ether, and polyallyl saccharose. The compound having two or more ethylenically unsaturated groups may be used alone or in combination of two or more types. Among them, from the viewpoint of suitably preparing a neutralized viscous liquid which has excellent dispersibility in water, has a viscosity that does not change greatly regardless of addition of an electrolyte, and has high transparency in the presence of an electrolyte, the compound having two or more ethylenically unsaturated groups preferably contains at least one of pentaerythritol polyallyl ether, diethylene glycol diallyl ether, polyethylene glycol allyl ether, and polyallyl saccharose.

In the alkyl-modified carboxyl group-containing copolymer of the present invention, the ratio of the compound having two or more ethylenically unsaturated groups is 0 to 0.1 parts by mass to 100 parts by mass of (meth)acrylic acid. From the viewpoint of suitably preparing a neutralized viscous liquid which has excellent dispersibility in water, has a viscosity that does not change greatly regardless of addition of an electrolyte, and has high transparency in the presence of an electrolyte, the lower limit of the ratio of the compound having two or more ethylenically unsaturated groups is 0 part by mass to 100 parts by mass of (meth)acrylic acid, and an upper limit thereof is 0.1 part by mass or less, preferably 0.05 parts by mass or less, more preferably 0.01 parts by mass or less. The range is preferably 0 to 0.05 parts by mass, more preferably 0 to 0.01 parts by mass.

The alkyl-modified carboxyl group-containing copolymer of the present invention may be copolymerized with the other monomer components other than (meth)acrylic acid, alkyl (meth)acrylate ester having an alkyl group having 18 to 24 carbon atoms, and a compound having two or more ethylenically unsaturated groups. The ratio of the other monomer components is, for example, 5.0 parts by mass or less to 100 parts by mass of (meth)acrylic acid.

The alkyl-modified carboxyl group-containing copolymer of the present invention contains a nonionic surfactant. More specifically, the nonionic surfactant is present on the surface or inside the alkyl-modified carboxyl group-containing copolymer, not as a monomer component. When the alkyl-modified carboxyl group-containing copolymer of the present invention is, for example, in the form of fine particles, the nonionic surfactant is contained on the surface or inside the fine particles.

The nonionic surfactant is composed of a hydrophobic moiety and a hydrophilic moiety.

Examples of the hydrophobic moiety include a polyhydric alcohol fatty acid ester and an addition polymer of a hydroxy fatty acid.

Suitable examples of the polyhydric alcohol moiety of the polyhydric alcohol fatty acid ester include one derived from polyhydric alcohols such as glycerin, polyglycerin, trimethylpropanol, sorbitol, and sorbitan. The polyhydric alcohol moieties may be present alone or in combinations of two or more. Suitable examples of the fatty acid moiety of the polyhydric alcohol fatty acid ester include one derived from fatty acids such as stearic acid, isostearic acid, and palmitic acid. The fatty acid moieties may be present alone or in combinations of two or more. Suitable examples of the polyhydric alcohol fatty acid ester include stearic acid esters, isostearic acid esters, palmitic acid esters, and hydrogenated castor oil derivatives.

Suitable examples of the addition polymer of the hydroxy fatty acid include addition polymers of 2-hydroxypalmitic acid, 16-hydroxypalmitic acid, and 12-hydroxystearic acid.

Examples of the hydrophilic moiety of the nonionic surfactant include an oxyalkylene chain in a nonionic surfactant. Suitable examples of the oxyalkylene chain include an oxyalkylene group represented by the following general formula:

$$-(CH_2-CHR^1-O)_n-$$

wherein $R^1$ represents a hydrogen atom, a methyl group, or an ethyl group; n represents an integer from 1 to 100; and where n is an integer of 2 or more, a plurality of $R^1$s may each be the same or different.

From the viewpoint of suitably preparing a neutralized viscous liquid which has excellent dispersibility in water, has a viscosity that does not change greatly regardless of addition of an electrolyte, and has high transparency in the presence of an electrolyte, the nonionic surfactant preferably has an HLB of 5 to 8.

From the viewpoint of suitably preparing a neutralized viscous liquid which has excellent dispersibility in water, has a viscosity that does not change greatly regardless of addition of an electrolyte, and has high transparency in the presence of an electrolyte, preferred specific examples of the nonionic surfactant include polyoxyethylene glyceryl triisostearate, polyoxyethylene hydrogenated castor oil derivatives, polyoxyethylene glycerin fatty acid esters, and polyoxyethylene trimethylol tristearate. Preferred specific examples of polyoxyethylene glycerin fatty acid esters include polyoxyethylene glyceryl monostearate, polyoxyethylene glyceryl distearate, polyoxyethylene glyceryl tristearate, polyoxyethylene glyceryl isostearate, polyoxyethylene glyceryl diisostearate, polyoxyethylene glyceryl triisostearate, polyoxyethylene monoisostearate hydrogenated castor oil, polyoxyethylene diisostearate hydrogenated castor oil, polyoxyethylene triisostearate hydrogenated castor oil, a block copolymer of 2-hydroxypalmitic acid and alkylene glycol, a block copolymer of 16-hydroxypalmitic acid and alkylene glycol, and a block copolymer of 12-hydroxystearic acid and alkylene glycol. The nonionic surfactant can be used solely, or two or more kinds thereof can be used in combination.

In the alkyl-modified carboxyl group-containing copolymer of the present invention, the ratio of the nonionic surfactant is 1.5 to 4.5 parts by mass to 100 parts by mass of (meth)acrylic acid. From the viewpoint of suitably preparing a neutralized viscous liquid which has excellent dispersibility in water, has a viscosity that does not change greatly regardless of addition of an electrolyte, and has high transparency in the presence of an electrolyte, the lower limit of the ratio of the nonionic surfactant is 1.5 parts by mass or more, preferably 2.0 parts by mass or more to 100 parts by mass of (meth)acrylic acid, and an upper limit thereof is 4.5 parts by mass or less, preferably 4.0 parts by mass or less. The preferred ranges for the ratios are 1.5 to 4.0 parts by mass, 2.0 to 4.5 parts by mass, and 2.0 to 4.0 parts by mass.

A lower limit of a viscosity A of the 1% by mass neutralized viscous liquid of the alkyl-modified carboxyl group-containing copolymer of the present invention 25° C. is preferably 5,000 mPa·s or more, more preferably 8000 mPa·s or more, and an upper limit thereof is preferably 15,000 mPa·s or less, more preferably 13,000 mPa·s or less. The preferred ranges are 5,000 to 15,000 mPa·s, 5,000 to 13,000 mPa·s, 8,000 to 15,000 mPa·s, and 8,000 to 13,000 mPa·s. In the alkyl-modified carboxyl group-containing copolymer of the present invention, since the amounts of the above-described monomer components and the nonionic surfactant are set to the above-described predetermined amounts, the value of the viscosity A of the 1% by mass neutralized viscous liquid can be suitably set, and the dispersibility in water can be made suitable.

Moreover, a lower limit of a viscosity ratio (viscosity B/viscosity A) of a viscosity B of an electrolyte-containing 1% neutralized viscous liquid, prepared by adding 1 part by mass of sodium chloride to 100 parts by mass of the 1% by mass neutralized viscous liquid to the viscosity A of the 1% by mass neutralized viscous liquid at 25° C. is preferably 0.5 or more, more preferably 1.0 or more, and an upper limit thereof is preferably 2.0 or less, more preferably 1.5 or less. The preferred ranges are 0.5 to 2.0, 0.5 to 1.5, 1.0 to 2.0, and 1.0 to 1.5. In the alkyl-modified carboxyl group-containing copolymer of the present invention, since the amounts of the monomer components and the nonionic surfactant are set to the above-described predetermined amounts, the viscosity ratio can be suitably set to such a range, and it is possible to suitably prepare a neutralized viscous liquid which has excellent dispersibility in water, has a viscosity that does not change greatly regardless of addition of an electrolyte, and has high transparency in the presence of an electrolyte.

An absolute value viscosity A-viscosity B of a difference between the viscosity A of the 1% by mass neutralized viscous liquid and the viscosity B of an electrolyte-containing 1% neutralized viscous liquid at 25° C. is preferably 10,000 mPa·s or less, more preferably 7,500 mPa·s or less, still more preferably 5,000 mPa·s or less. In the alkyl-modified carboxyl group-containing copolymer of the present invention, since the amounts of the monomer components and the nonionic surfactant are set to the above-described predetermined amounts, the viscosity difference can be suitably set to such a value, and it is possible to suitably prepare a neutralized viscous liquid which has excellent dispersibility in water, has a viscosity that does not change greatly regardless of addition of an electrolyte, and has high transparency in the presence of an electrolyte.

A lower limit of the viscosity B of the electrolyte-containing 1% neutralized viscous liquid of the alkyl-modified carboxyl group-containing copolymer of the present invention at 25° C. is preferably 5,000 mPa·s or more, more preferably 7,500 mPa·s or more, still more preferably 10,000 Pa·s or more, and an upper limit thereof is preferably 17,500 mPa·s or less, more preferably 15,000 mPa·s or less. The preferred ranges are 5,000 to 20,000 mPa·s, 5,000 to 17,500 mPa·s, 5,000 to 15,000 mPa·s, 7,500 to 20,000 mPa·s, 7,500 to 17,500 mPa·s, 7,500 to 15,000 mPa·s, 10,000 to 20,000 mPa·s, 10,000 to 17,500 mPa·s, and 10,000 to 15,000 mPa·s.

The viscosity A of the 1% by mass neutralized viscous liquid and the viscosity B of the electrolyte-containing 1% neutralized viscous liquid are each a value obtained by measuring the viscosity at 25° C. after one minute rotating with a rotational speed of 20 rotations per minute by using a rotational viscometer with a spindle rotor No. 6 with respect to each neutralized viscous liquid.

A lower limit of a light transmittance X of the 1% by mass neutralized viscous liquid of the alkyl-modified carboxyl group-containing copolymer of the present invention is preferably 90% or more, more preferably 94% or more, still more preferably 96% or more, and an upper limit hereof is preferably 100% or less. The preferred ranges are 90 to 100%, 94 to 100%, and 96 to 100%. In the alkyl-modified carboxyl group-containing copolymer of the present invention, since the amounts of the monomer components and the nonionic surfactant are set to the above-described predetermined amounts, the light transmittance X of the 1% by mass neutralized viscous liquid can be suitably set in such a range, and a neutralized viscous liquid having high transparency can be obtained.

A lower lit of a light transmittance Y of the electrolyte-containing 1% neutralized viscous liquid of the alkyl-modified carboxyl group-containing copolymer of the present invention is preferably 90% or more, more preferably 92% or more, still more preferably 94% or more, and an upper limit thereof is preferably 100% or less. The preferred ranges are 90 to 100%, 92 100%, and 94 to 100%. In the alkyl-modified carboxyl group-containing copolymer of the present invention, since the amounts of the monomer components and the nonionic surfactant are set to the above-described predetermined amounts, the light transmittance Y of the electrolyte-containing 1% neutralized viscous liquid can be suitably set in such a range, and a neutralized viscous liquid having high transparency in the presence of an electrolyte can be obtained.

The light transmittance X of the 1% by mass neutralized viscous liquid and the light transmittance Y of the electrolyte-containing 1% neutralized viscous liquid were values obtained by feeding each neutralized viscous liquid to a centrifugal separator, defoaming the liquid by operation at 2000 rotations per minute for 20 minutes, and then measuring the light transmittance using a cell having an optical path length of 1 cm at a measurement wavelength of 425 nm.

In the alkyl-modified carboxyl group-containing copolymer of the present invention, the time required for uniform dispersion in water as measured by the following measurement method is preferably 30 minutes or less, more preferably 25 minutes or less.

(Method of Measuring Time Required for Uniform Dispersion in Water)

495 g of distilled water at 25° C. is added to a glass beaker having a diameter of 11 cm and a capacity of 1000 mL, and the distilled water is stirred at 1000 rpm using a stirrer having three blades with a diameter of 3 cm. 5 g of the alkyl-modified carboxyl group-containing copolymer is gradually added to the continuously stirred water, and the time until the copolymer is uniformly dispersed in the water without any lumps is visually confirmed. In order to prevent overlooking of the alkyl-modified carboxyl group-containing copolymer before the copolymer is thoroughly dispersed, the dispersion is passed through a filter cloth having an opening of 142 μm. When a block of the alkyl-modified carboxyl group-containing copolymer is confirmed on the filter cloth, it is judged that the alkyl-modified carboxyl group-containing copolymer is not uniformly dispersed, and the measurement is performed again from the beginning. If the time until uniform dispersion is 30 minutes or less, uniform dispersibility in water can be evaluated as excellent.

The alkyl-modified carboxyl group-containing copolymer of the present invention is in a form of fine particles, for example. For the particle diameter of fine particles, from the viewpoint of improving dispersibility in water, for example, 90% or more of particles have a particle diameter in a range of 1 to 30 μm.

As a method for preparing the alkyl-modified carboxyl group-containing copolymer of the present invention, there is a method including a process of copolymerizing at least a (meth)acrylic acid, an alkyl (meth)acrylate ester having an alkyl group having 18 to 24 carbon atoms, and optionally a compound having two or more ethylenically unsaturated groups in the presence of a nonionic surfactant. The copolymerization method is a general method for copolymerizing monomers, such as a method for stirring monomer components in a solvent under an inactive gas atmosphere and performing copolymerization with a polymerization initiator.

The inert gas for obtaining an inert gas atmosphere includes a nitrogen gas, an argon gas, and the like.

The solvent is not particularly limited, so long as the solvent dissolves at least each monomer component, but the solvent does not dissolve the resulting alkyl-modified carboxyl group-containing copolymer and does not inhibit the polymerization reaction. Specific examples of the solvent include normal-pentane, normal-hexane, normal-heptane, normal-octane, isooctane, cyclopentane, methylcyclopentane, cyclohexane, methylcyclohexane, benzene, toluene, xylene, chlorobenzene, ethylene dichloride, ethyl acetate, isopropyl acetate, ethyl methyl ketone and isobutyl methyl ketone. The solvent may be used alone or in combinations of two or more. Among these solvents, normal-hexane, normal-heptane, cyclohexane, ethylene dichloride, ethyl acetate, and the like are suitably used from the viewpoint of stable quality and easy availability.

The amount of the solvent used is preferably 300 to 5,000 parts by mass to 100 parts by mass of (meth)acrylic acid from the viewpoints of adjustment of a salt-resistant viscosity of the alkyl-modified carboxyl group-containing copolymer to the above range, improvement of stirring operability, and economical efficiency.

For example, the polymerization initiator is preferably a radical polymerization initiator. Specific examples of the polymerization initiator include 2,2'-azobis(methyl isobutyrate), α,α'-azoisobutyronitrile, 2,2'-azobis-2,4-dimethylvaleronitrile, dimethyl-2,2'-azobisisobutyrate, benzoyl peroxide, lauroyl peroxide, cumene hydroperoxide and tert-butyl hydroperoxide. The polymerization initiator may be used alone or in combinations of two or more.

The amount of the polymerization initiator used is preferably 0.00003 to 0.002 mol per 1 mol of (meth)acrylic acid. When the amount of the polymerization initiator used is 0.00003 mol or more, the reaction rate is not slow, which is economical. When the amount of the polymerization initiator used is 0.002 mol or less, it is possible to suppress that the polymerization vigorously progresses.

The polymerization temperature is preferably about 50° C. to 90° C., more preferably about 55° C. to 75° C. When the polymerization temperature is 50° C. or higher, the polymerization rate is not slow, which is economical. When the polymerization temperature is 90° C. or lower, it is possible to suppress that the polymerization vigorously progresses.

The polymerization time varies depending on the polymerization temperature and the like, but is usually about 0.5 to 5 hours.

The alkyl-modified carboxyl group-containing copolymer of the present invention can be obtained by heating a slurry liquid after polymerization to, for example, 80° C. to 130° C. to remove the solvent. When the heating temperature is 80° C. or higher, the drying time can be shortened. When the heating temperature is 130° C. or lower, it is possible to further suppress agglomeration of the alkyl-modified carboxyl group-containing copolymer when the obtained alkyl-modified carboxyl group-containing copolymer is dispersed in water.

Since the neutralized viscous liquid obtained using the alkyl-modified carboxyl group-containing copolymer of the present invention has a viscosity that does not change greatly regardless of addition of an electrolyte, and has high transparency in the presence of an electrolyte, the neutralized viscous liquid can be suitably used as a thickener for cosmetics. Specifically, the alkyl-modified carboxyl group-containing copolymer of the present invention can be suitably used as a thickener for cosmetics by, for example, being dispersed in pure water such as deionized water, neutralized with an alkali, and prepared as a neutralized viscous liquid having a concentration of about 1% by mass and a pH of 6.5 to 7.5. That is, the present invention can provide a thickener containing the alkyl-modified carboxyl group-containing copolymer of the present invention.

The alkali used for neutralization includes an alkali metal hydroxide such as sodium hydroxide, and amines such as triethanolamine and diisopropanolamine, and among them, sodium hydroxide is suitably used.

Examples of cosmetics to which the thickener of the present invention can be suitably used include lotion, emulsion, essence, cream, cream pack, massage cream, cleansing cream, cleansing gel, facial wash foam, sunscreen, styling gel, eyeliner, mascara, lipstick, and foundation.

EXAMPLES

Hereinafter, the present invention will be described in detail with reference to examples and comparative examples. However, the present invention is not limited to the examples.

Example 1

A 500-mL four-necked flask equipped with a stirrer, a thermometer, a nitrogen inlet tube, and a condenser was charged with 45 g of acrylic acid, 1.35 g of BLEMMER VMA70 (manufactured by NOF Corporation: a mixture containing 10 to 20 parts by mass of stearyl methacrylate, 10 to 20 parts by mass of eicosanyl methacrylate, 59 to 80 parts by mass of behenyl methacrylate, and 1% by mass or less of tetracosanyl methacrylate) as an alkyl (meth)acrylate ester having an alkyl group having 18 to 24 carbon atoms, 0.116 g of 2,2'-azobismethylisobutyrate as a radical polymerization initiator, and 230.9 g of normal-hexane as a reaction solvent. Subsequently, the solution was homogeneously mixed while stirring, and a nitrogen gas was then blown into the solution in order to remove oxygen existing in the upper spatial region of the reaction vessel (four-necked flask), raw materials and the reaction solvents. Next, the solution was heated to 60 to 65° C. in a nitrogen atmosphere. 2 hours after the temperature of the solution reached 60° C., 0.9 g of a block copolymer of 12-hydroxystearic acid and polyoxyethylene (Hypermer B246 from Croda) as the nonionic surfactant was charged into the reaction vessel. Thereafter, the temperature of the solution was maintained at 60 to 65° C. for 3 hours after reaching 60° C. Thereafter, the formed slurry was heated to 100° C. to distill off normal-hexane, further dried for 8 hours by setting the set temperature of a heating device to 115° C. and setting the set pressure of a decompression device to 10 mmHg, to thereby give 41 g of white fine particles of an alkyl-modified carboxyl group-containing copolymer.

Example 2

The same procedures as in Example 1 were carried out, except for adding 0.0045 g of pentaerythritol polyallyl ether as a compound having at least two ethylenically unsaturated groups at the time of preparation of the raw material before heating, to give 43 g of white fine particles of an alkyl-modified carboxy group-containing copolymer.

Example 3

The same procedures as in Example 2 were carried out, except for changing the amount of BLEMMER VMA70 (manufactured by NOF Corporation: a mixture containing 10 to 20 parts by mass of stearyl methacrylate, 10 to 20 parts by mass of eicosanyl methacrylate, 59 to 80 parts by mass of behenyl methacrylate, and 1% by mass or less of tetracosanyl methacrylate) used to 1.575 g and changing the amount of a block copolymer of 12-hydroxystearic acid and polyoxyethylene (Hypermer B246 from Croda) used to 1.575 g, to give 42 g of white fine particles of an alkyl-modified carboxyl group-containing copolymer.

Example 4

The same procedures as in Example 2 were carried out, except for using 1.35 g of polyoxyethylene (30) hydrogenated castor oil triisostearate (EMALEX RWIS-330 from Nihon Emulsion Co., Ltd.) instead of a block copolymer of 12-hydroxystearic acid and polyoxyethylene (Hypermer 8246 from Croda), to give 43 g of white fine particles of an alkyl-modified carboxyl group-containing copolymer.

Example 5

The same procedures as in Example 2 were carried out, except for using 1.35 g of polyoxyethylene (20) hydrogenated castor oil triisostearate (EMALEX RWIS-320 from Nihon Emulsion Co., Ltd.) instead of a block copolymer of 12-hydroxystearic acid and polyoxyethylene (Hypermer B246 from Croda), to give 43 g of white fine particles of an alkyl-modified carboxyl group-containing copolymer.

Example 6

The same procedures as in Example 2 were carried out, except for changing the amount of BLEMMER VMA70 (manufactured by NOF Corporation: a mixture containing 10 to 20 parts by mass of stearyl methacrylate, 10 to 20 parts by mass of eicosanyl methacrylate, 59 to 80 parts by mass of behenyl methacrylate, and 1% by mass or less of tetracosanyl methacrylate) used to 1.125 g and changing the amount of a block copolymer of 12-hydroxystearic acid and polyoxyethylene (Hypermer B246 from Croda) used to 1.800 g, to give 42 g of white fine particles of an alkyl-modified carboxyl group-containing copolymer.

Example 7

The same procedures as in Example 1 were carried out, except for changing the amount of BLEMMER VMA70 (manufactured by NOF Corporation: a mixture containing 10 to 20 parts by mass of stearyl methacrylate, 10 to 20 parts by mass of eicosanyl methacrylate, 59 to 80 parts by mass of behenyl methacrylate, and 1% by mass or less of tetracosanyl methacrylate) used to 1.800 g and changing the amount of a block copolymer of 12-hydroxystearic acid and polyoxyethylene (Hypermer 9246 from Croda) used to 0.675 g, to give 41 g of white fine particles of an alkyl-modified carboxyl group-containing copolymer.

Comparative Example 1

The same procedures as in Example 2 were carried out, except for changing the amount of a block copolymer of 12-hydroxystearic acid and polyoxyethylene (Hypermer B246 from Croda) used to 0.450 g, to give 40 g of white fine particles of an alkyl-modified carboxyl group-containing copolymer.

Comparative Example 2

The same procedures as in Example 2 were carried out, except for changing the amount of a block copolymer of 12-hydroxystearic acid and polyoxyethylene (Hypermer B246 from Croda) used to 2.250 g, to give 43 g of white fine particles of an alkyl-modified carboxyl group-containing copolymer.

Comparative Example 3

The same procedures as in Example 2 were carried out, except for changing the amount of BLEMMER VMA70 (manufactured by NOF Corporation: a mixture containing 10 to 20 parts by mass of stearyl methacrylate, 10 to 20 parts by mass of eicosanyl methacrylate, 59 to 80 parts by mass of behenyl methacrylate, and 1% by mass or less of tetracosanyl methacrylate) used to 0.900 g, changing the amount of pentaerythritol polyallyl ether used as a compound having at least two ethylenically unsaturated groups to 0.068 g, and changing the amount of a block copolymer of 12-hydroxystearic acid and polyoxyethylene (Hypermer B246 from Croda) used to 1.350 g, to give 43 g of white fine particles of an alkyl-modified carboxyl group-containing copolymer.

Comparative Example 4

The same procedures as in Example 2 were carried out, except for changing the amount of BLEMMER VMA70 (manufactured by NOF Corporation: a mixture containing 10 to 20 parts by mass of stearyl methacrylate, 10 to 20 parts by mass of eicosanyl methacrylate, 59 to 80 parts by mass of behenyl methacrylate, and 1% by mass or less of tetracosanyl methacrylate) used to 2.475 g and changing the amount of a block copolymer of 12-hydroxystearic acid and polyoxyethylene (Hypermer B246 from Croda) used to 1.350 g, to give 43 g of white fine particles of an alkyl-modified carboxyl group-containing copolymer.

Comparative Example 5

The same procedures as in Example 2 were carried out, except for changing the amount of BLEMMER VMA70 (manufactured by NOF Corporation: a mixture containing 10 to 20 parts by mass of stearyl methacrylate, 10 to 20 parts by mass of eicosanyl methacrylate, 59 to 80 parts by mass of behenyl methacrylate, and 1% by mass or less of tetracosanyl methacrylate) used to 0.450 g and changing the amount of a block copolymer of 12-hydroxystearic acid and polyoxyethylene (Hypermer B246 from Croda) used to 1.350 g, to give 43 g of white fine particles of an alkyl-modified carboxyl group-containing copolymer.

<Evaluation>

Each alkyl-modified carboxyl group-containing copolymer obtained above was evaluated by the following methods. The results are shown in Table 1.

(1) Dispersibility in Water 495 g of distilled water at 25° C. was added to a glass beaker having a diameter of 11 cm and a capacity of 1000 mL, and the distilled water was stirred at 1000 rpm using a stirrer having three blades with a diameter of 3 cm. 5 g of each alkyl-modified carboxyl group-containing copolymer obtained above was gradually added to the continuously stirred water, and the time until the copolymer was uniformly dispersed without any lumps was visually confirmed. In order to prevent overlooking of the alkyl-modified carboxyl group-containing copolymer before the copolymer was thoroughly dispersed, the dispersion was passed through a filter cloth having an opening of 142 μm. When a block of the alkyl-modified carboxyl group-containing copolymer was confirmed on the filter cloth, it was judged that the alkyl-modified carboxyl group-containing copolymer was not uniformly dispersed, and the measurement was performed again from the beginning. If the time until uniform dispersion is 30 minutes or less, uniform dispersibility in water can be evaluated as excellent.

(2) Preparation of 1% by Mass Neutralized Viscous Liquid 283 g of each alkyl-modified carboxyl group-containing copolymer dispersion obtained above was weighed into a 500 mL beaker and added with 17 g of 6% by mass sodium hydroxide while stirring to give a 1% by mass neutralized viscous liquid having a pH of 6.5 to 7.5. The 1% by mass neutralized viscous liquid was allowed to stand in a constant temperature water bath at 25° C. until the temperature reached 25° C., and used as an evaluation sample.

(3) Preparation of Electrolyte-Containing 1% Neutralized Viscous Liquid.

In the same manner as in "(2) Preparation of 1% by mass neutralized viscous liquid", each 1% by mass neutralized viscous liquid was obtained. Next, while continuing stirring of the 1% by mass neutralized viscous liquid, 3 g of sodium chloride was added, and the stirring was continued until the viscous liquid became uniform, thereby obtaining an electrolyte-containing 1% neutralized viscous liquid containing 1% by mass of sodium chloride. The electrolyte-containing 1% neutralized viscous liquid was allowed to stand in a constant temperature water bath at 25° C. until the temperature reached 25° C., and used as an evaluation sample.

(4) Viscosity Measurement

The viscosity after 1 minute for each of the evaluation samples obtained above was measured at 25° C. using a rotary viscometer with a rotational speed of a spindle rotor No. 6 of 20 rotations per minute. The viscosity A (mPa·s) of the 1% by mass neutralized viscous liquid, the viscosity B (mPa·s) of the electrolyte-containing 1% neutralized viscous liquid, the viscosity ratio (viscosity B/viscosity A), and the absolute value |viscosity A-viscosity B| (mPa·s) of the viscosity difference are shown in Table 1.

(5) Light Transmittance Measurement

Each of the evaluation samples was defoamed by operation at 2000 rotations per minute for 20 minutes in a centrifugal separator, and then light transmittance was measured using a cell having an optical path length of 1 cm at a measurement wavelength of 425 nm. Usually, when the light transmittance is 90% or more, it can be said to be transparent visually. The light transmittance X (%) of the 1% by mass neutralized viscous liquid and the light transmittance V (%) of the electrolyte-containing 1% neutralized viscous liquid are shown in Table 1.

TABLE 1

| Component | Unit | Example 1 | Example 2 | Example 3 | Example 4 | Example 5 | Example 6 | Example 7 | Comparative Example 1 | Comparative Example 2 | Comparative Example 3 | Comparative Example 4 | Comparative Example 5 |
|---|---|---|---|---|---|---|---|---|---|---|---|---|---|
| Acrylic acid | Parts by mass | 100 | 100 | 100 | 100 | 100 | 100 | 100 | 00 | 100 | 100 | 100 | 100 |
| Alkyl (meth)acrylate ester having an alkyl group having 18 to 24 carbon atoms | Parts by mass | 3.0 | 3.0 | 3.5 | 3.0 | 3.0 | 2.5 | 4.0 | 3.0 | 3.0 | 2.0 | 5.5 | 1.0 |
| Compound having two or more ethylenically unsaturated groups | Parts by mass | 0 | 0.01 | 0.01 | 0.01 | 0.01 | 0.01 | 0 | 0.01 | 0.01 | 0.15 | 0.01 | 0.01 |
| Nonionic surfactant | Type | HYP246 | HYP246 | HYP246 | RWIS-330 | RWIS-320 | HYP246 | HYP246 | HYP246 | HYP246 | HYP246 | HYP246 | HYP246 |
| | Parts by mass | 2.0 | 2.0 | 3.5 | 3.0 | 3.0 | 4.0 | 1.5 | 1.0 | 5.0 | 3.0 | 3.0 | 3.0 |
| Viscosity A of 1% neutralized viscous liquid | mPa·s | 8,200 | 8,660 | 11,720 | 10,740 | 10,300 | 8,820 | 13,500 | 7,120 | 11,300 | 5,200 | 16,960 | 2,300 |
| Viscosity B of electrolyte-containing 1% neutralized viscous liquid | mPa·s | 16,100 | 16,540 | 13,040 | 14,300 | 14,260 | 11,100 | 11,000 | 15,420 | 10,700 | 10,400 | 8,520 | 4,200 |
| Light transmittance X of 1% neutralized viscous liquid | % | 96.1 | 96.1 | 97.5 | 100.0 | 100.0 | 96.2 | 95.2 | 96.7 | 95.7 | 95.0 | 95.6 | 95.6 |
| Light transmittance Y of electrolyte-containing 1% neutralized | % | 92.8 | 92.8 | 90.0 | 94.6 | 92.7 | 91.6 | 90.0 | 95.4 | 78.5 | 75.0 | 69.0 | 93.0 |

TABLE 1-continued

| Component | Unit | Example 1 | Example 2 | Example 3 | Example 4 | Example 5 | Example 6 | Example 7 | Comparative Example 1 | Comparative Example 2 | Comparative Example 3 | Comparative Example 4 | Comparative Example 5 |
|---|---|---|---|---|---|---|---|---|---|---|---|---|---|
| viscous liquid | | | | | | | | | | | | | |
| Viscosity ratio (viscosity B/viscosity A) | | 2.0 | 1.9 | 1.1 | 1.3 | 1.4 | 1.3 | 0.8 | 2.2 | 0.9 | 2.0 | 0.5 | 1.8 |
| Absolute value \|viscosity A-viscosity B\| of viscosity difference | mPa·s | 7,900 | 7,880 | 1,320 | 3,560 | 3,960 | 2,280 | 2,500 | 8,300 | 600 | 5,200 | 8,440 | 1,900 |
| Dispersibility in water (time required for uniform dispersion in water) | min | 28 | 27 | 22 | 24 | 24 | 20 | 29 | 45 | 16 | 25 | 23 | 35 |

In Table 1, HYP246 refers to a block copolymer of 12-hydroxystearic acid and polyoxyethylene (Hypermer B246 from Croda). RWIS-330 refers to polyoxyethylene (30) hydrogenated castor oil triisostearate (EMALEX RWIS-330 from Nihon Emulsion Co., Ltd.). Similarly, RWIS-320 refers to polyoxyethylene (20) hydrogenated castor oil triisostearate (EMALEX RWIS-320 from Nihon Emulsion Co., Ltd.).

The invention claimed is:

1. An alkyl-modified carboxyl group-containing copolymer being a copolymer of 100 parts by mass of a (meth) acrylic acid, 1.5 to 4.5 parts by mass of an alkyl (meth) acrylate ester having an alkyl group having 18 to 24 carbon atoms, and 0 to 0.1 parts by mass of a compound having two or more ethylenically unsaturated groups, the alkyl-modified carboxyl group-containing copolymer comprising 1.5 to 4.5 parts by mass of a nonionic surfactant
wherein the nonionic surfactant is composed of a hydrophobic moiety and a hydrophilic moiety, and
wherein the hydrophobic moiety is a type selected from the group consisting of a polyhydric alcohol fatty acid ester and an addition polymer of a hydroxy fatty acid, and
wherein the nonionic surfactant has a hydrophilic-lipophilic balance (HLB) of 5 to 8.

2. The alkyl-modified carboxyl group-containing copolymer according to claim 1, wherein a light transmittance X of a 1% by mass neutralized viscous liquid of the alkyl-modified carboxyl group-containing copolymer is 90% or more.

3. The alkyl-modified carboxyl group-containing copolymer according to claim 1, wherein a light transmittance Y of an electrolyte-containing 1% neutralized viscous liquid prepared by adding 1 part by mass of sodium chloride to 100 parts by mass of the 1% by mass neutralized viscous liquid of the alkyl-modified carboxyl group-containing copolymer is 90% or more.

4. The alkyl-modified carboxyl group-containing copolymer according to claim 1, wherein a viscosity A of the 1% by mass neutralized viscous liquid of the alkyl-modified carboxyl group-containing copolymer is 5,000 mPa·s or more at 25° C.

5. The alkyl-modified carboxyl group-containing copolymer according to claim 1, wherein a viscosity ratio (viscosity B/viscosity A) of a viscosity B of an electrolyte-containing 1% neutralized viscous liquid, prepared by adding 1 part by mass of sodium chloride to 100 parts by mass of the 1% by mass neutralized viscous liquid of the alkyl-modified carboxyl group-containing copolymer, to the viscosity A of the 1% by mass neutralized viscous liquid is in a range of 0.5 to 2.0 at 25° C.

6. The alkyl-modified carboxyl group-containing copolymer according to claim 1, wherein an absolute value |viscosity A-viscosity B| of a difference between the viscosity A of the 1% by mass neutralized viscous liquid of the alkyl-modified carboxyl group-containing copolymer and the viscosity B of the electrolyte-containing 1% neutralized viscous liquid prepared by adding 1 part by mass of sodium chloride to 100 parts by mass of the 1% by mass neutralized viscous liquid is 10,000 mPa·s or less.

7. The alkyl-modified carboxyl group-containing copolymer according to claim 1, wherein the compound having two or more ethylenically unsaturated groups is at least one selected from the group consisting of pentaerythritol polyallyl ether, diethylene glycol diallyl ether, polyethylene glycol allyl ether, and polyallyl saccharose.

8. The alkyl-modified carboxyl group-containing copolymer according to claim 1, being in a form of fine particles.

9. A thickener comprising the alkyl-modified carboxyl group-containing copolymer according to claim 1.

10. A method for preparing the alkyl-modified carboxyl group-containing copolymer according to claim 1, the method comprising copolymerizing a (meth)acrylic acid, an alkyl (meth)acrylate ester having an alkyl group having 18 to 24 carbon atoms, and optionally a compound having two or more ethylenically unsaturated groups in the presence of a nonionic surfactant.

* * * * *